(12) United States Patent
Tazawa et al.

(10) Patent No.: US 12,076,710 B2
(45) Date of Patent: Sep. 3, 2024

(54) CATALYST AND CATALYST GROUP

(71) Applicant: Mitsubishi Chemical Corporation, Chiyoda-ku (JP)

(72) Inventors: Kazuharu Tazawa, Tokyo (JP); Takanori Taniguchi, Tokyo (JP); Takuya Nakamura, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 18/174,695

(22) Filed: Feb. 27, 2023

(65) Prior Publication Data
US 2023/0219070 A1 Jul. 13, 2023

Related U.S. Application Data

(60) Division of application No. 16/580,327, filed on Sep. 24, 2019, now Pat. No. 11,628,425, which is a
(Continued)

(30) Foreign Application Priority Data

Mar. 27, 2017 (JP) .................................. 2017-061962
Apr. 27, 2017 (JP) .................................. 2017-088648
(Continued)

(51) Int. Cl.
*B01J 23/887* (2006.01)
*B01J 21/08* (2006.01)
(Continued)

(52) U.S. Cl.
CPC ........... *B01J 23/8877* (2013.01); *B01J 21/08* (2013.01); *B01J 23/002* (2013.01);
(Continued)

(58) Field of Classification Search
None
See application file for complete search history.

(56) References Cited

U.S. PATENT DOCUMENTS 4,282,116 A 8/1981 Reuter et al.
4,656,157 A 4/1987 Hofmann et al.
(Continued)

FOREIGN PATENT DOCUMENTS

CN 1697697 A 11/2005
CN 1697695 A 11/2006
(Continued)

OTHER PUBLICATIONS

Combined Chinese Office Action and Search Report issued Feb. 15, 2022 in corresponding Chinese Patent Application No. 201880021054.2 (with machine-generated English translation).
(Continued)

*Primary Examiner* — Coris Fung
*Assistant Examiner* — Keling Zhang
(74) *Attorney, Agent, or Firm* — Oblon, McClelland, Maier & Neustadt, L.L.P.

(57) ABSTRACT

A ring-shaped catalyst may have a straight body part and a hollow body part, which is used when a gas-phase catalytic oxidation reaction of a material substance is conducted to produce a target substance, wherein a length of the straight body part is shorter than a length of the hollow body part and at least at one end part, a region from an end part of the straight body part to an end part of the hollow body part is concavely curved.

20 Claims, 4 Drawing Sheets

Related U.S. Application Data continuation of application No. PCT/JP2018/012233, filed on Mar. 26, 2018.

(30) Foreign Application Priority Data

| | | | |
|---|---|---|---|
| May 16, 2017 | (JP) | ................................. | 2017-097655 |
| May 16, 2017 | (JP) | ................................. | 2017-097656 |
| Jan. 29, 2018 | (JP) | ................................. | 2018-012547 |
| Jan. 29, 2018 | (JP) | ................................. | 2018-012548 |
| Jan. 29, 2018 | (JP) | ................................. | 2018-012549 |
| Jan. 29, 2018 | (JP) | ................................. | 2018-012550 |

(51) Int. Cl.

| | |
|---|---|
| *B01J 23/00* | (2006.01) |
| *B01J 23/843* | (2006.01) |
| *B01J 23/883* | (2006.01) |
| *B01J 35/00* | (2006.01) |
| *B01J 35/30* | (2024.01) |
| *B01J 35/40* | (2024.01) |
| *B01J 35/50* | (2024.01) |
| *B01J 35/61* | (2024.01) |
| *B01J 37/00* | (2006.01) |
| *B01J 37/02* | (2006.01) |
| *B01J 37/03* | (2006.01) |
| *B01J 37/06* | (2006.01) |
| *B01J 37/08* | (2006.01) |
| *C07C 45/35* | (2006.01) |
| *C07C 51/25* | (2006.01) |

(52) U.S. Cl.
CPC ......... *B01J 23/8435* (2013.01); *B01J 23/883* (2013.01); *B01J 23/8876* (2013.01); *B01J 35/00* (2013.01); *B01J 35/30* (2024.01); *B01J 35/40* (2024.01); *B01J 35/50* (2024.01); *B01J 35/613* (2024.01); *B01J 37/0036* (2013.01); *B01J 37/0221* (2013.01); *B01J 37/0228* (2013.01); *B01J 37/0236* (2013.01); *B01J 37/0244* (2013.01); *B01J 37/038* (2013.01); *B01J 37/06* (2013.01); *B01J 37/08* (2013.01); *C07C 45/35* (2013.01); *C07C 51/252* (2013.01); *B01J 2523/00* (2013.01)

(56) References Cited

U.S. PATENT DOCUMENTS

| | | | |
|---|---|---|---|
| 4,902,823 | A | 2/1990 | Wunder et al. |
| 2001/0029235 | A1 | 10/2001 | Walsdorff et al. |
| 2005/0065371 | A1 | 3/2005 | Petzoldt et al. |
| 2005/0159620 | A1 | 7/2005 | Teshgahara et al. |
| 2008/0008877 | A1 | 1/2008 | Harth et al. |
| 2010/0016840 | A1 | 1/2010 | Guckel et al. |
| 2011/0105790 | A1 | 5/2011 | Hagemeyer et al. |
| 2011/0137078 | A1 | 6/2011 | Nakahara et al. |
| 2011/0275856 | A1 | 11/2011 | Karpov et al. |
| 2012/0063324 | A1 | 3/2012 | Kim et al. |
| 2012/0063349 | A1 | 3/2012 | Kim et al. |
| 2012/0063350 | A1 | 3/2012 | Kim et al. |
| 2012/0063351 | A1 | 3/2012 | Kim et al. |
| 2012/0078933 | A1 | 3/2012 | Kim et al. |
| 2013/0310604 | A1 | 11/2013 | Kurakami et al. |
| 2013/0338378 | A1 | 12/2013 | Reitzmann et al. |
| 2014/0187817 | A1 | 7/2014 | Balduf et al. |
| 2016/0029363 | A1 | 1/2016 | Kim et al. |
| 2018/0234962 | A1 | 8/2018 | Kim et al. |
| 2019/0223173 | A1 | 7/2019 | Kim et al. |

FOREIGN PATENT DOCUMENTS

| | | |
|---|---|---|
| CN | 102046289 A | 5/2011 |
| CN | 102627537 A | 8/2012 |
| DE | 10 2010 052 126 A1 | 5/2012 |
| EP | 0 184 790 A2 | 6/1986 |
| JP | 52-76553 U | 6/1977 |
| JP | 55-139834 A | 11/1980 |
| JP | 61-141933 A | 6/1986 |
| JP | 1-228940 A | 9/1989 |
| JP | 5-317713 A | 12/1993 |
| JP | 6-145093 A | 5/1994 |
| JP | 2001-293376 A | 10/2001 |
| JP | 2007-505740 A | 3/2007 |
| JP | 2017-80731 A | 5/2017 |
| RU | 2 377 068 C2 | 11/2007 |
| RU | 2 315 656 C1 | 1/2008 |
| RU | 2 393 014 C2 | 12/2009 |
| RU | 2 592 607 C2 | 6/2014 |
| TW | 201323400 A1 | 6/2013 |
| WO | 2005/030393 A1 | 4/2005 |
| WO | 2007/059974 A1 | 5/2007 |
| WO | 2009/147965 A1 | 10/2009 |
| WO | 2018/021241 A1 | 2/2018 |

OTHER PUBLICATIONS

Combined Russian Office Action and Search Report issued Jun. 4, 2020 in Russian Patent Application No. 2019130056 (with English translation).

Indian Office Action Issued Dec. 16, 2020 in Indian Patent Application No. 201917038634 (with English translation).

Extended European Search Report issued Feb. 24, 2020 in corresponding European Patent Application No. 18776404.8.

International Search Report issued Jun. 19, 2018 in PCT/JP2018/012233, filed Mar. 26, 2018 (with English translation).

Written Opinion issued Jun. 19, 2018 in PCT/JP2018/012233, filed Mar. 26, 2018.

Taiwanese Office Action issued May 15, 2019 in Taiwan Application 107110521 (with English Translation).

CATALYST AND CATALYST GROUP

CROSS-REFERENCE TO RELATED APPLICATIONS

The present application is a division of U.S. application Ser. No. 16/580,327, filed on Sep. 24, 2019, and published as US 2020/0016577 A1 on Jan. 16, 2020, which was a bypass continuation of international application PCT/JP2018/012233, filed on Mar. 26, 2018, and claims the benefit of the filing date of Japanese Appl. No. 2017-061962, filed on Mar. 27, 2017, Japanese Appl. No. 2017-088648, filed on Apr. 27, 2017, Japanese Appl. No. 2017-097655, filed on May 16, 2017, Japanese Appl. No. 2017-097656, filed on May 16, 2017, Japanese Appl. No. 2018-012547, filed on Jan. 29, 2018. Japanese Appl. No. 2018-012548, filed on Jan. 29, 2018, Japanese Appl. No. 2018-012549, filed on Jan. 29, 2018, and Japanese Appl. No. 2018-012550, filed on Jan. 29, 2018, the content of each of which is incorporated by reference.

TECHNICAL FIELD

The present invention is related to a catalyst and a catalyst group. More specifically, the present invention is related to a catalyst and a catalyst group which are used when a gas-phase catalytic oxidation reaction of an olefin or a tertiary butanol is conducted to produce a corresponding unsaturated aldehyde and/or unsaturated carboxylic acid, and a catalyst and a catalyst group which are used when gas-phase catalytic oxidation of an unsaturated aldehyde is conducted to produce a corresponding unsaturated carboxylic acid.

BACKGROUND ART

Heretofore, various proposals have been made for the shape of a catalyst used when a gas-phase catalytic oxidation reaction of an olefin or a tertiary butanol is conducted to produce a corresponding unsaturated aldehyde and/or unsaturated carboxylic acid, or a catalyst used when gas-phase catalytic oxidation of an unsaturated aldehyde such as acrolein is conducted to produce a corresponding unsaturated carboxylic acid.

For example, in Patent Literature 1, a molded catalyst for a heterogeneous catalytic reaction, which is molded in a hollow cylindrical body shape with an end face of the hollow cylindrical body shape being curved, is described as a catalyst used for selective oxidation from a (meth)acrolein to a (meth)acrylic acid. In Patent Literature 2, a ring-like unsupported catalyst containing at least Mo, Bi and Fe having specific length, outer diameter, wall thickness, in which an end face is curved, is described as a catalyst for producing an acrolein from propylene, etc. In Patent Literature 3, a ring-shaped catalyst is described as a catalyst used when acrylic acid is synthesized from acrolein by gas-phase catalytic oxidation. In addition, Patent Literature 4 describes a supported catalyst for producing a phthalic anhydride containing vanadium and titanium and/or zirconium, in which both front surfaces of an annular support are chamfered obliquely from inside to outside and the length of the cylindrical outer wall is shortened by at least 20% in comparison to the length of the cylindrical inner wall.

BACKGROUND ART LITERATURE

Patent Literature

Patent Literature 1: JP-A-S61-141933
Patent Literature 2: JP-A-2007-505740
Patent Literature 3: JP-A-H05-317713
Patent Literature 4: JP-A-S55-139834

SUMMARY OF INVENTION

Technical Problem

However, these conventionally known catalysts have a problem that at the production of a target substance by a gas-phase catalytic oxidation reaction of a raw material in a reactor filled with the catalyst, the pressure loss is high, the conversion rate of the raw material is low, and the selectivity for the corresponding target substance is low, which decreases the yield.

For example, a ring-shaped catalyst may not uniformly fill a reactor, and the reaction field may become uneven, which results in the possibility of occurrence of reduction in the conversion rate and selectivity. In addition, in the case where the hollow cylindrical body-shaped catalyst having a curved end face, since the catalyst surface area relative to the catalyst volume is small and there is a small number of reaction active sites, a reaction efficiency becomes low, which results in the possibility of reducing the conversion rate and selectivity.

Furthermore, in the production of an unsaturated aldehyde and/or an unsaturated carboxylic acid, a carbide is deposited on the catalyst surface. The deposition (coking) of the carbide on the catalyst surface is likely to occur due to a decrease in the gas volume in a reaction tube involving high pressure loss of a multitubular reactor. Once coking occurs, this leads to a vicious cycle where the pressure loss is further increased and in turn, deposition of the carbide on the catalyst surface is more accelerated, and finally, there is a possibility that the reaction should be forced to stop.

The present invention has been made to solve these problems.

More specifically, an object of the present invention is to provide a catalyst and a catalyst group, ensuring that when a gas-phase catalytic oxidation reaction of an olefin or a tertiary butanol is conducted to produce a corresponding unsaturated aldehyde and/or unsaturated carboxylic acid, the pressure loss can be reduced to keep the gas volume high, coking can thereby be suppressed, and a corresponding unsaturated aldehyde and/or unsaturated carboxylic acid can be produced in high yield.

Another object of the present invention is to provide a catalyst and a catalyst group, ensuring that when gas-phase catalytic oxidation of an unsaturated aldehyde such as acrolein is conducted to produce a corresponding unsaturated carboxylic acid, the pressure loss can be reduced to keep the gas volume high, coking can thereby be suppressed, and a corresponding unsaturated carboxylic acid can be produced in high yield.

Solution to Problem

As a result of many intensive studies to solve those problems, inventors of the present invention have found that the above-described objects can be solved by the following catalyst or catalyst group, and have accomplished the present invention.

[1] A ring-shaped catalyst having a straight body part and a hollow body part, which is used when a gas-phase catalytic oxidation reaction of an olefin or a tertiary butanol is conducted to produce a corresponding unsaturated aldehyde and/or unsaturated carboxylic acid, wherein:

a length of the straight body part is shorter than a length of the hollow body part and at least at one end part, a region from an end part of the straight body part to an end part of the hollow body part is concavely curved.

[2] A ring-shaped catalyst having a straight body part and a hollow body part, which is used when gas-phase catalytic oxidation of an unsaturated aldehyde is conducted to produce a corresponding unsaturated carboxylic acid, wherein:

a length of the straight body part is shorter than a length of the hollow body part and at least at one end part, a region from an end part of the straight body part to an end part of the hollow body part is concavely curved.

[3] The catalyst according to [1] or [2], wherein the straight body part is present between a surface including one end part of the hollow body part and a surface including another end part of the hollow body part.

[4] The catalyst according to any one of [1] to [3], wherein at least at one end part, a ratio of a maximum distance (mm) between a surface connecting the end part of the straight body part to the end part of the hollow body part and the concavely curved surface to a distance (mm) between the end part of the straight body part and the end part of the hollow body part is 0.01 or more and 0.2 or less.

[5] The catalyst according to any one of [1] to [4], wherein at both end parts, the region from the end part of the straight body part to the end part of the hollow body part is concavely curved.

[6] The catalyst according to any one of [1] to [5], wherein an angle between the straight body part and a line connecting the end part of the straight body part to the end part of the hollow body part is from 45 to 85°.

[7] The catalyst according to any one of [1] to [6], wherein a ratio (a/b) of an outer diameter a (mm) in the straight body part to an inner diameter b (mm) in a region including the hollow body part in an axial direction is 2.3 or more, a ratio (H/b) of a straight body part length H (mm) to an inner diameter b (mm) in a region including the hollow body part in the axial direction is 1.3 or more, the straight body part length H (mm) is from 2 to 11 mm, and the outer diameter a (mm) in the straight body part is from 2 to 11 mm.

[8] A production method of acrolein and/or acrylic acid, containing conducting gas-phase catalytic oxidation of a raw material mixed gas containing propylene and an oxygen-containing gas in the presence of the catalyst according to [1].

[9] A production method of acrylic acid, containing conducting gas-phase catalytic oxidation of a raw material mixed gas containing acrolein and an oxygen-containing gas in the presence of the catalyst according to [2].

[10] A catalyst group containing 200 or more ring-shaped catalysts each having a straight body part and a hollow body part, which is used when a gas-phase catalytic oxidation reaction of an olefin or a tertiary butanol is conducted to produce a corresponding unsaturated aldehyde and/or unsaturated carboxylic acid, wherein the catalyst group satisfies the following (1) and (2):

(1) the catalyst group contains a catalyst (A) in which a length of the straight body part is shorter than a length of the hollow body part, the straight body part is present between a surface including one end part of the hollow body part and a surface including another end part of the hollow body part, and at least at one end part, a region from an end part of the straight body part to an end pan of the hollow body part is linear and/or concavely curved, and (2) an upward ratio by a shaking test of the catalyst group is 70% or less:

(Measurement Method of an Upward Ratio by Shaking Test of Catalyst Group)

100 ring-shaped catalysts randomly extracted from the catalyst group are placed in a stainless steel tray (width: 2% mm, depth: 231 mm, height: 49 mm), the stainless steel tray is mounted in a digital shaker FLK-L330-D (manufactured by AS ONE Corporation) and after shaking for 1 minute under a condition of a reciprocatory shaking width of 10 mm and a shaking speed of 350 reciprocations/min, a number of catalysts having an upward hollow body part per 100 ring-shaped catalysts is defined as the upward ratio.

[11] A catalyst group containing 20 or more ring-shaped catalysts each having a straight body pan and a hollow body part, which is used when gas-phase catalytic oxidation of an unsaturated aldehyde is conducted to produce a corresponding unsaturated carboxylic acid, wherein the catalyst group satisfies the following (1) and (2):

(1) the catalyst group contains a catalyst (A) in which the length of the straight body part is shorter than the length of the hollow body part, the straight body part is present between a surface including one end pan of the hollow body part and a surface including another end part of the hollow body part, and at least at one end part, the region from an end part of the straight body part to an end part of the hollow body part is linear and/or concavely curved, and (2) an upward ratio by a shaking test of the catalyst group is 70% or less:

(Measurement Method of Upward Ratio by Shaking Test of Catalyst Group)

100 ring-shaped catalysts randomly extracted from the catalyst group are placed in a stainless steel tray (width: 296 mm, depth: 231 mm, height: 49 mm), the stainless steel tray is mounted in a digital shaker FLK-L330-D (manufactured by AS ONE Corporation) and after shaking for 1 minute under a condition of a reciprocatory shaking width of 10 mm and a shaking speed of 350 reciprocations/min, a number of catalysts having an upward hollow body part per 100 ring-shaped catalysts is defined as the upward ratio.

[12] The catalyst group according to [10] or [11], wherein in the catalyst (A), a ratio of a maximum distance (mm) between a surface connecting the end part of the straight body part to the end part of the hollow body pan and the linear or concavely curved surface to a distance (mm) between the end part of the straight body part and the end part of the hollow body part is 0 or more and 0.2 or less.

[13] The catalyst group according to any one of [10] to [12], wherein at both end parts of the catalyst (A), the region from the end pan of the straight body pan to the end part of the hollow body part is linear and/or concavely curved.

[14] A production method of acrolein and/or acrylic acid, containing conducting gas-phase catalytic oxidation of propylene in the presence of the catalyst group according to [10].

[15] A production method of acrylic acid, containing conducting gas-phase catalytic oxidation of acrolein in the presence of the catalyst group according to [11].

Effects of Invention

According to a catalyst of the first embodiment of the present invention or a catalyst group of the third embodiment of the present invention, when gas-phase catalytic oxidation of an olefin such as propylene or a tertiary butanol with an oxygen-containing gas is conducted using a reactor filled with the catalyst or catalyst group to produce an unsaturated aldehyde such as acrolein and/or an unsaturated carboxylic acid such as acrylic acid, a pressure loss can be reduced and a gas volume can thereby be kept high. Accordingly, coking can be suppressed, and an unsaturated aldehyde such as acrolein and/or an unsaturated carboxylic acid such as acrylic acid can be produced in high yield from an olefin such as propylene or a tertiary butanol. Furthermore, even in a coked state, the effect of reducing the pressure loss is maintained, in comparison with a catalyst having a conventional shape, and therefore, the frequency of decoking can be decreased.

According to a catalyst of the second embodiment of the present invention or a catalyst group of the fourth embodiment of the present invention, when gas-phase catalytic oxidation of an unsaturated aldehyde such as acrolein with an oxygen-containing gas is conducted using a reactor filled with the catalyst or catalyst group to produce an unsaturated carboxylic acid, a pressure loss can be reduced and a gas volume can thereby be kept high. Accordingly, coking can be suppressed, and an unsaturated carboxylic acid such as acrylic acid can be produced in high yield from an unsaturated aldehyde such as acrolein. Furthermore, even in a coked state, the effect of reducing the pressure loss is maintained, in comparison with a catalyst having a conventional shape, and therefore, a frequency of decoking can be decreased.

DESCRIPTION OF EMBODIMENTS

The embodiments of the present invention are described in detail below. However, the present invention is not limited to the embodiments described below.

In the present description, each of the elements of molybdenum (Mo), bismuth (Bi), silicon (Si), cobalt (Co), nickel (Ni), iron (Fe), sodium (Na), potassium (K), rubidium (Rb), cesium (Cs), thallium (TI), boron (B), phosphorus (P), arsenic (As), magnesium (Mg), calcium (Ca), zinc (Zn), cerium (Ce), and samarium (Sm) is sometimes described using the element symbol in the parenthesis.

In the present description, an "end part" of the ring-shaped catalyst indicates a region around an end in the opening direction (axial direction) of the ring-shaped catalyst. The ring-shaped catalyst has two end pars (upper end and lower end).

In the present description, a "straight body part" of the ring-shaped catalyst indicates a portion having a constant outer diameter in the ring-shaped catalyst. A "length of the straight body part" indicates the length in the axial direction of the straight body part. An "end part of the straight body part" indicates an outer edge part of the ring-shaped catalyst at an axial-direction end of the straight body part. The ring-shaped catalyst has two end parts (upper end and lower end) of the straight body part.

Figure 1A:
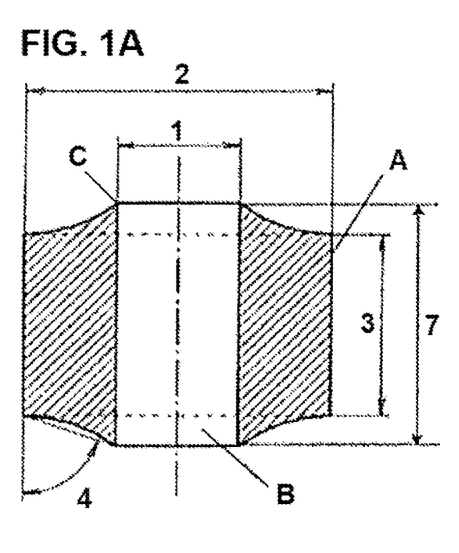
FIG. 1A is a transverse cross-sectional view in one example of the catalysts of the first and second embodiments of the present invention.
Figure 1B:
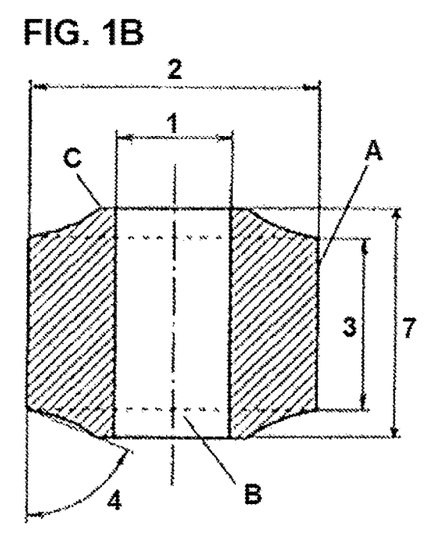
FIG. 1B is a transverse cross-sectional view in another example of the catalysts of the first and second embodiments of the present invention.

In the present description, a "hollow body part" of the ring-shaped catalyst indicates a portion having a constant inner diameter in the hollow portion of the ring-shaped catalyst. A "length of the hollow body part" indicates the length in the axial direction of the hollow body part. An "end part of the hollow body part" indicates an inner edge part of the ring-shaped catalyst at an axial-direction end of the hollow body part but in a case where the ring-shaped catalyst has a bottom surface part as illustrated in FIG. 1B, indicates an outer edge part of the ring-shaped catalyst at an axial-direction end of the hollow body part. The ring-shaped catalyst has two end parts (upper end and lower end) of the hollow body part.

First and Second Embodiments

In the following, the catalyst (catalyst particle) of the first embodiment of the present invention and the catalyst (catalyst particle) of the second embodiment of the present invention are described in detail. FIG. 1A illustrates one example of a shape of the catalysts according to the first and second embodiments of the present invention.

The catalyst of the first embodiment of the present invention is a ring-shaped catalyst having a straight body part and a hollow body part, which is used when a gas-phase catalytic oxidation reaction of an olefin or a tertiary butanol is conducted to produce a corresponding unsaturated aldehyde and/or unsaturated carboxylic acid, wherein a length of the straight body part is shorter than a length of the hollow body part and at least at one end part, a region from an end part of the straight body part to an end part of the hollow body part is concavely curved.

The catalyst of the second embodiment of the present invention is a ring-shaped catalyst having a straight body part and a hollow body part, which is used when gas-phase catalytic oxidation of an unsaturated aldehyde is conducted to produce a corresponding unsaturated carboxylic acid, wherein a length of the straight body part is shorter than a length of the hollow body part and at least at one end part, a region from an end part of the straight body part to an end part of the hollow body part is concavely curved.

In this connection, in the following, an olefin or tertiary butanol in the use of the catalyst of the first embodiment of the present invention and the later-described catalyst group of the third embodiment, and an unsaturated aldehyde in the use of the catalyst of the second embodiment of the present invention and the later-described catalyst group of the fourth embodiment are sometimes collectively referred to as a raw material substance.

In addition, an unsaturated aldehyde and/or an unsaturated carboxylic acid in the use of the catalyst of the first embodiment of the present invention and the later-described catalyst group of the third embodiment, and an unsaturated carboxylic acid in the use of the catalyst of the second embodiment of the present invention and the later-described catalyst group of the fourth embodiment are sometimes collectively referred to as a target substance.

The catalysts of the first and second embodiments of the present invention have the above-described configurations, so that when a reactor is filled with the catalyst and gas-phase catalytic oxidation of a raw material substance with an oxygen-containing gas is conducted to produce a target substance, the pressure loss is reduced and the target substance can be produced in high yield.

In the catalyst of the present embodiment, the straight body part is preferably present between a surface including one end part of the hollow body part and a surface including another end part of the hollow body part. More specifically, the hollow body part has two end parts, i.e., an upper end and a lower end, as described above, and the straight body part is preferably present between a surface including the upper end of the hollow body part and a surface including the lower end of the hollow body part. By virtue of having such a structure, a pressure loss at the time of filling a reactor with the catalyst and producing a target substance by gas-phase catalytic oxidation of a raw material substance with an oxygen-containing gas can be reduced, and the target substance can be produced in high yield.

In the catalyst of the present embodiment, a length of the straight body part is shorter than a length of the hollow body part and at least at one end part, a region from an end part of the straight body part to an end part of the hollow body part is concavely curved. FIG. 1A and FIG. 1B illustrate an example of the catalyst of the present embodiment. Here, FIG. 1B is an example of the catalyst where the concave-curved surface from the straight body part does not reach the hollow body part but stays at the bottom surface part of the ring shape and in the case where the ring-shaped catalyst has a bottom surface part, as described above, the outer edge part of the ring-shaped catalyst at an axial-direction end of the hollow body part is an end part of the hollow body part, and such an example is encompassed by the catalyst of the present embodiment. The catalyst of the present embodiment has a large surface area relative to the volume, providing a large number of reaction active sites, and therefore, as in FIG. 1A, preferably does not have a bottom surface part.

At least at one end part of the catalyst of the present embodiment, a ratio (hereinafter, sometimes referred to as "degree of concave curving") of a maximum distance (mm) between a surface connecting the end part of the straight body part to the end part of the hollow body part and the concavely curved surface (hereinafter, sometimes referred to as "concave-curved surface") to a distance (mm) between the end part of the straight body part and the end part of the hollow body part is preferably 0.01 or more and 0.2 or less, more preferably 0.02 or more and 0.15 or less, and still more preferably 0.05 or more and 0.1 or less. Within such a range, the pressure loss at the time of filling a reactor with the catalyst and producing a target substance by gas-phase catalytic oxidation of a raw material substance with an oxygen-containing gas can be reduced, and the target substance can be produced in high yield.

Figure 2A:
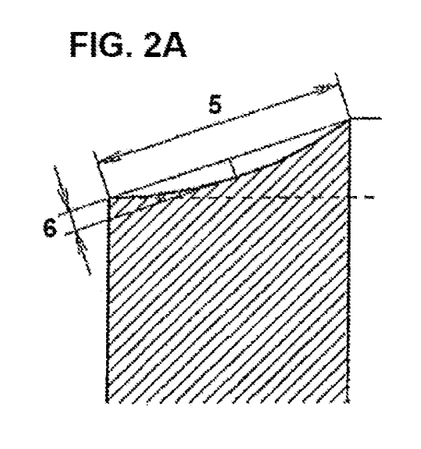
FIG. 2A is a transverse cross-sectional view of an end part in the example illustrated in FIG. 1A of the catalysts of the first and second embodiments of the present invention.
Figure 2B:
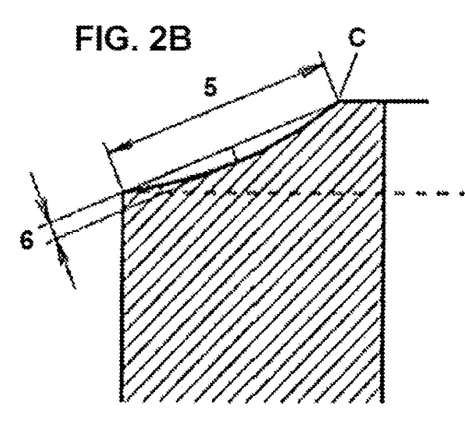
FIG. 2B is a transverse cross-sectional view of an end part in the example illustrated in FIG. 1B of the catalysts of the first and second embodiments of the present invention.

In this connection, as apparent from FIG. 2A and FIG. 2B, the maximum distance between a surface connecting the end part of the straight body part to the end part of the hollow body part and the concave-curved surface is a length of a portion having a longest distance between the surface connecting the end part of the straight body part to the end part of the hollow body part and the concave-curved surface.

In the catalyst of the present embodiment, it is preferred that at both end parts, the region from the end part of the straight body part to the end part of the hollow body part is concavely curved. In this case, good fluidity is provided to the catalyst and at the time of filling a reactor with the catalyst by means of a funnel, etc., bridging of the catalyst in the funnel is prevented, and uniform filling inside of a reaction tube with the catalyst is achieved, which makes it possible to shorten the filling time. Furthermore, the pressure loss at the time of producing a target substance by gas-phase catalytic oxidation of a raw material substance with an oxygen-containing gas after filling a reactor with the catalyst can be reduced, and the target substance can be produced in high yield.

The angle between the straight body part and a line connecting the end part of the straight body part to the end part of the hollow body part is preferably from 45 to 85°, more preferably from 55 to 80°, and still more preferably from 65 to 75°. In this case, the pressure loss at the time of filling a reactor with the catalyst and then producing a target substance by gas-phase catalytic oxidation of a raw material substance with an oxygen-containing gas can be reduced, and the target substance can be produced in high yield.

In the catalyst of the present invention, it is preferred that a ratio (a/b) of the outer diameter a in the straight body part (hereinafter, sometimes simply referred to as "outer diameter a" or "a"; the unit is mm) to the inner diameter b in a region including the hollow body part in the axial direction (hereinafter, sometimes simply referred to as "inner diameter b" or "b"; the unit is mm) is 2.3 or more, a ratio (H/b) of the straight body part length H (mm) to the inner diameter b (mm) is 1.3 or more, the straight body part length H (mm) is from 2 to 11 mm, and the outer diameter a (mm) is from 2 to 11 mm. By virtue of having such a structure, breaking of the catalyst during filling of a reactor can be suppressed, the pressure loss at the time of producing a target substance by gas-phase catalytic oxidation of a raw material substance with an oxygen-containing gas can be reduced, and the target substance can be produced in high yield.

The ratio: a/b is more preferably 2.35 or more, still more preferably 2.4 or more, yet still more preferably 2.45 or more, and particularly preferably 2.5 or more. Although the upper limit is not particularly limited, in view of catalyst strength, it is preferably 3.5 or less.

The ratio: H/b is more preferably 1.35 or more, still more preferably 1.4 or more, yet still more preferably 1.45 or more, and particularly preferably 1.5 or more. Although the upper limit is not particularly limited, in view of the effect of preventing bridging during filling of a multitubular reactor, it is preferably 2.5 or less.

H is more preferably from 2 to 10 mm, still more preferably from 2.3 to 9 mm, yet still more preferably from 2.6 to 7 mm, and particularly preferably from 3 to 5 mm.

a is more preferably from 2 to 10 mm, still more preferably from 3 to 9 mm, yet still more preferably from 4 to 7 mm, and particularly preferably from 4 to 5.6 mm.

Furthermore, the ratio (a/H) of the outer diameter a (mm) to the straight body part length H (mm) is preferably 1.47 or more, still more preferably 1.50 or more, yet still more preferably 1.53 or more, and particularly preferably 1.56 or more. Although the upper limit is not particularly limited, it is preferably 2.5 or less. By virtue of having such a structure, the pressure loss at the time of filling a reactor with the catalyst and producing a target substance by gas-phase catalytic oxidation of a raw material substance with an oxygen-containing gas can be reduced, and the target substance can be produced in high yield.

The catalyst of the first embodiment of the present invention is preferably a catalyst containing at least molybdenum and bismuth. A catalyst containing such two components can be adapted to uses of the catalyst of the first embodiment of the present invention and among others, the catalyst is preferably a catalyst represented by the following formula (1):

$$Mo_aBi_bCo_cNi_dFe_eX_fY_gZ_hQ_iSi_jO_k \qquad (1)$$

(in the formula (1), X is at least one element selected from the group consisting of Na, K, Rb, Cs and Ti, Y is at least one element selected from the group consisting of B, P, As and W, Z is at least one element selected from the group consisting of Mg, Ca, Zn, Ce and Sm, Q is a halogen atom such as chlorine, a to k represent an atomic ratio of respective elements and when a=12, are in the ranges of $0.5 \leq b \leq 7$, $0 \leq c \leq 10$, $0 \leq d \leq 10$, $0 \leq e \leq 3$, $0 \leq f \leq 3$, $0 \leq g \leq 3$, $0 \leq h \leq 1$, $0 \leq i \leq 0.5$, and $0 \leq j \leq 40$, and k is a numerical value for satisfying the oxidation state of other elements).

The catalyst of the second embodiment of the present invention is preferably a catalyst containing at least molybdenum and vanadium. A catalyst containing such two components can be adapted to uses of the catalyst of the second embodiment of the present invention and among others, the catalyst is preferably a catalyst represented by the following formula (2):

$$Mo_aV_bCu_cSb_dSi_eX_fY_gZ_hO_i \qquad (2)$$

(in formula (2), X is at least one element selected from the group consisting of Nb and W, Y is at least one element selected from the group consisting of Mg, Ca, Sr, Ba and Zn, Z is at least one element selected from the group consisting of Fe, Co, Ni, and Bi, a to i represent an atomic ratio of respective elements and when a=12, are in the ranges of $0 < b \leq 12$, $0 < c \leq 12$, $0 \leq d \leq 500$, $0 \leq e \leq 500$, $0 \leq f \leq 12$, $0 \leq g \leq 8$, and $0 \leq h \leq 500$, and i is a numerical value for satisfying the oxidation state of other elements).

The catalysts of the first and second embodiments of the present invention are produced, for example, as follows.

Firstly, a raw material compound containing respective element components above of the catalyst is appropriately dissolved or dispersed in an aqueous medium in an amount required according to the composition produced, and a mixed solution containing catalyst components or its aqueous slurry is thereby produced. As the raw materials of respective catalyst components, nitrate, ammonium salt, hydroxide, oxide, sulfate, carbonate, halide, acetate, etc. containing each element is used. For example, as the molybdenum, ammonium paramolybdate, molybdenum trioxide, molybdenum chloride, etc. are used. As the bismuth, bismuth chloride, bismuth nitrate, bismuth oxide, bismuth subcarbonate, etc. are used. As the vanadium, ammonium vanadate, vanadium pentoxide, vanadium oxalate, vanadium sulfate, etc. are used.

A mixed solution or aqueous slurry containing the above-described catalyst components is preferably thoroughly stirred and mixed so as to prevent uneven distribution of each component.

Subsequently, the mixed solution or aqueous slurry containing the catalyst components is dried to form a powder. Although drying can be conducted by various methods and includes, for example, drying by a spray drier, a slurry drier, a drum drier, etc., in particular, drying by a spray drier is preferred.

Thereafter, the powder obtained by drying is molded into a ring shape to obtain the catalyst of the present embodiment. Although a molding method into a ring shape is not particularly limited, tablet molding, extrusion molding, etc. are preferred. In particular, for the reason that the angle between the straight body part and a line connecting the end part of the straight body part to the end part of the hollow body part or the degree of concave curving can be easily controlled, tablet molding is preferred. In the molding, a molding aid may be used. Preferable molding aids are silica, graphite, crystalline cellulose, cellulose, starch, polyvinyl alcohol, and stearic acid. The molding aid can be used usually in an amount of approximately from 1 to 50 parts by weight per 100 parts by weight of the powder. In addition, if desired, an inorganic fiber such as ceramic fiber and whisker can also be used as a material for enhancing the mechanical strength of the catalyst. A used amount of the each fiber is usually from 1 to 30 parts by weight per 100 parts by weight of the powder.

Third and Fourth Embodiments

In the following, the catalyst group (catalyst particle group) of the third embodiment of the present invention and the catalyst group (catalyst particle group) of the fourth embodiment of the present invention are described in detail.

The catalyst group of the third embodiment of the present invention is a catalyst group containing 200 or more ring-shaped catalysts each having the straight body part and the hollow body part, which is used when a gas-phase catalytic oxidation reaction of an olefin or a tertiary butanol is conducted to produce a corresponding unsaturated aldehyde and/or unsaturated carboxylic acid, wherein the catalyst group satisfies the following (1) and (2).

The catalyst group of the fourth embodiment of the present invention is a catalyst group containing 200 or more ring-shaped catalysts each having the straight body part and the hollow body part, which is used when gas-phase catalytic oxidation of an unsaturated aldehyde is conducted to produce a corresponding unsaturated carboxylic acid, wherein the catalyst group satisfies the following (1) and (2).

(1) The catalyst group contains a catalyst in which the length of the straight body part is shorter than the length of the hollow body part, the straight body part is present between a surface including one end part of the hollow body pan and a surface including another end part of the hollow body part, and at least at one end part, the region from the end part of the straight body part to the end pan of the hollow body part is linear and/or concavely curved.

(2) An upward ratio by a shaking test of the catalyst group is 70% or less.

(Measurement Method of Upward Ratio by Shaking Test of Catalyst Group)

100 Ring-shaped catalysts randomly extracted from the catalyst group are placed in a stainless steel tray (width: 296 mm, depth: 231 mm, height: 49 mm), the stainless steel tray is mounted in a digital shaker FLK-L330-D (manufactured by AS ONE Corporation) and after shaking for 1 minute under the conditions of a reciprocatory shaking width of 10 mm and a shaking speed of 350 reciprocations/min, the number of catalysts having an upward hollow body part per 100 ring-shaped catalysts is defined as the upward ratio.

In this connection, the "upward hollow body pan" means that the opening direction (axial direction) of the ring-shaped catalyst is perpendicular to the bottom surface of the stainless steel tray.

In the following, the catalyst in which the length of the straight body part is shorter than the length of the hollow body part, the straight body part is present between a surface including one end part of the hollow body part and a surface including another end part of the hollow body part, and at least at one end part, the region from the end part of the straight body part to the end part of the hollow body part is linear and/or concavely curved, is sometimes referred to as "catalyst (A)".

The catalyst group of the present embodiment is a catalyst group containing 200 or more ring-shaped catalysts each having a straight body part and a hollow body part. The number of ring-shaped catalysts contained in the catalyst group of the present embodiment is preferably 220 or more, more preferably 250 or more, still more preferably 300 or more, yet still more preferably 1,000 or more, conspicuously preferably 2,000 or more, and particularly preferably 3,000 or more. Within this range, the pressure loss at the time of filling a reaction tube, etc. with the catalyst group and producing a target substance by gas-phase catalytic oxidation of a raw material substance with an oxygen-containing gas can be reduced, the conversion rate of the raw material substance can be increased, and the target substance can be produced with high selectivity. In this connection, in view of the filling amount into a reactor such as reaction tube, the upper limit is preferably 20,000 or less, more preferably 15,000 or less, and still more preferably 12,000 or less.

A ratio of the number of catalysts (A) to the total number of ring-shaped catalysts in the catalyst group of the present embodiment is preferably 10% or more, more preferably 50% or more, still more preferably 80% or more, and particularly preferably 95% or more. Within this range, the pressure loss at the time of filling a reactor such as reaction tube with the catalyst group and producing a target substance by gas-phase catalytic oxidation of a raw material substance with an oxygen-containing gas can be reduced, and the target substance can be produced in high yield.

The upward ratio by a shaking test of the catalyst group of the present embodiment is 70% or less, preferably 50% or less, more preferably 40% or less, still more preferably 30% or less, and particularly preferably 25% or less. The lower limit of the upward ratio is preferably 1% or more, more preferably 3% or more, and even more preferably 5% or more. Within this range, the pressure loss at the time of filling a reactor such as reaction tube with the catalyst group and producing a target substance by gas-phase catalytic oxidation of a raw material substance with an oxygen-containing gas can be reduced, and the target substance can be produced in high yield.

Figure 3A:
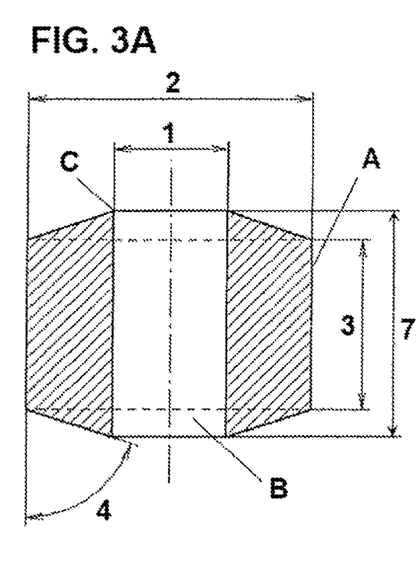
FIG. 3A is a transverse cross-sectional view in one example of the catalyst (A) in the catalyst group of the third and fourth embodiments of the present invention.
Figure 3B:
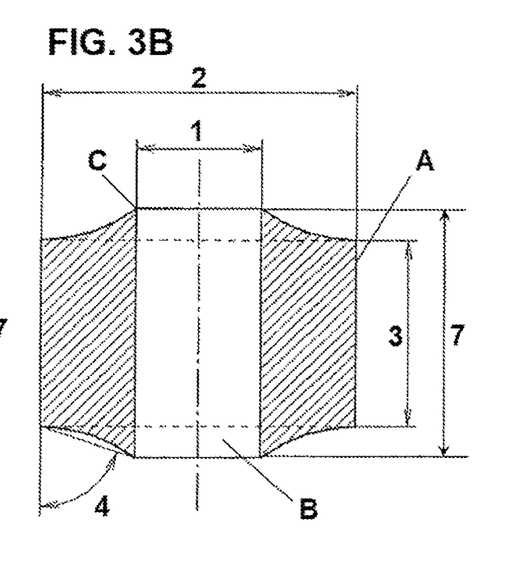
FIG. 3B is a transverse cross-sectional view in another example of the catalyst (A) in the catalyst group of the third and fourth embodiments of the present invention.
Figure 5A:
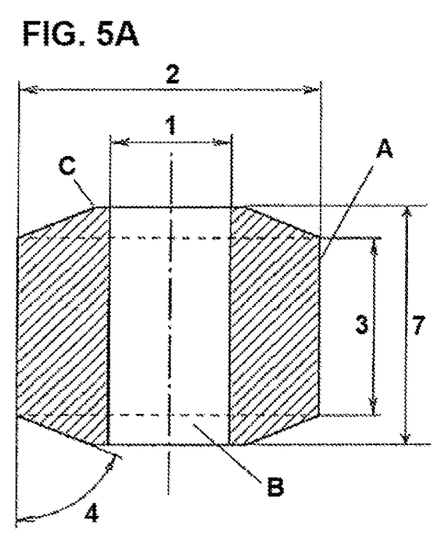
FIG. 5A is a transverse cross-sectional view in one example of the catalyst (A) in the catalyst group of the third and fourth embodiments of the present invention.
Figure 5B:
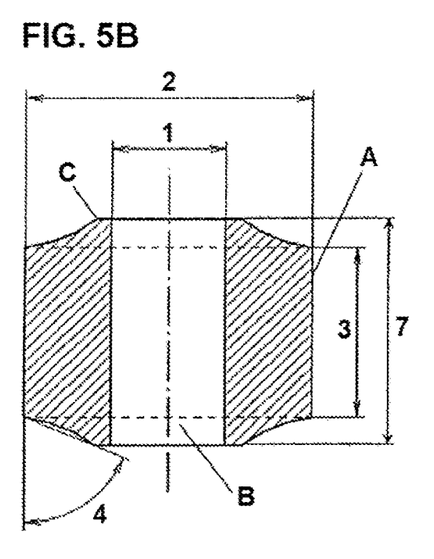
FIG. 5B is a transverse cross-sectional view in another example of the catalyst (A) in the catalyst group of the third and fourth embodiments of the present invention.

FIG. 3A and FIG. 5A are an example of the catalyst (A) in which the region from the end part of the straight body part to the end part of the hollow body part is linear, and FIG. 3B and FIG. 5B are an example of the catalyst (A) in which the region from the end pan of the straight body part to the end part of the hollow body part is concavely curved.

In this connection, the example illustrated in FIG. 5A and FIG. 5B is an example where the linear or concavely curved surface from the straight body part does not reach the hollow body part but stays at the bottom surface part of the ring shape and in the case where the ring-shaped catalyst has a bottom surface part, as described above, the outer edge part of the ring-shaped catalyst at an axial-direction end of the hollow body part is the end part of the hollow body pan, and such an example is encompassed by the catalyst (A).

The catalyst (A) contained in the catalyst group of the present embodiment has a large surface area relative to the volume and therefore, as in the example illustrated in FIG. 3A and FIG. 3B, a catalyst (A) not having a bottom surface part is preferred.

When the proportion (hereinafter, sometimes referred to as "proportion of concave curve") of the number of end parts in which the region from the end part of the straight body part to the end part of the hollow body part is concavely curved, relative to the total number of end parts of the catalysts (A) is in a specific range, the pressure loss at the time of producing a target substance by gas-phase catalytic oxidation of a raw material substance by using the catalyst group of the present embodiment can be reduced, and the target substance can be produced in high yield. In this connection, since two end parts are present per one catalyst (A), the total number of end parts of the catalysts (A) is twice the number of catalysts (A).

In the catalyst group of the present embodiment, the proportion of concave carve is preferably 40% or more, more preferably 50% or more, still more preferably 60% or more, yet still more preferably 70% or more, even yet still more preferably 80% or more, far preferably 90% or more, yet far preferably 95% or more, and most preferably 100%.

In this connection, for example, when all catalysts (A) have a structure where at least at one end part, the region from the end part of the straight body part to the end part of the hollow body pan is linear and at another end pan, the region from the end part of the straight body part to the end part of the hollow body part is concavely curved, the proportion of concave curve is 50%. In addition, when half of the catalysts (A) have a structure in which at both end parts, the region from the end part of the straight body part to the end part of the hollow body part is linear, and another half has a structure in which at both end parts, the region from the end part of the straight body part to the end part of the hollow body part is concavely curved, the proportion of concave curve is 50% as well.

In the catalyst (A), the ratio (hereinafter, sometimes referred to as "degree of concave curving") of the maximum distance (mm) between a surface connecting the end part of the straight body part to the end part of the hollow body part and the concavely curved surface (hereinafter, sometimes referred to as "concave-curved surface") to the distance (mm) between the end part of the straight body part and the end part of the hollow body part is preferably 0 or more and 0.2 or less, more preferably 0 or more and 0.15 or less, and still more preferably 0 or more and 0.1 or less. Within this range, the pressure loss at the time of filling a reactor such as reaction tube with the catalyst group and producing a target substance by gas-phase catalytic oxidation of a raw material substance can be reduced, and the target substance can be produced in high yield.

Figure 4A:
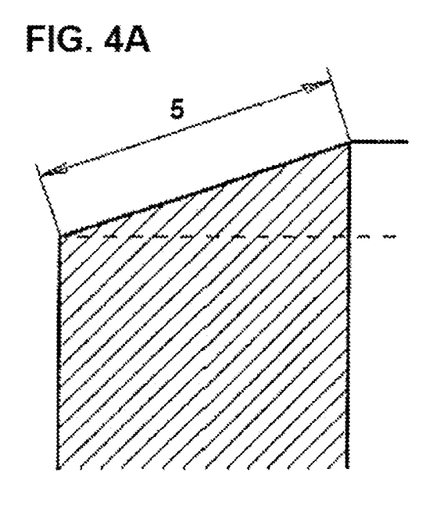
FIG. 4A is a transverse cross-sectional view of an end part in the example illustrated in FIG. 3A of the catalyst (A) in the catalyst group of the third and fourth embodiments of the present invention.
Figure 4B:
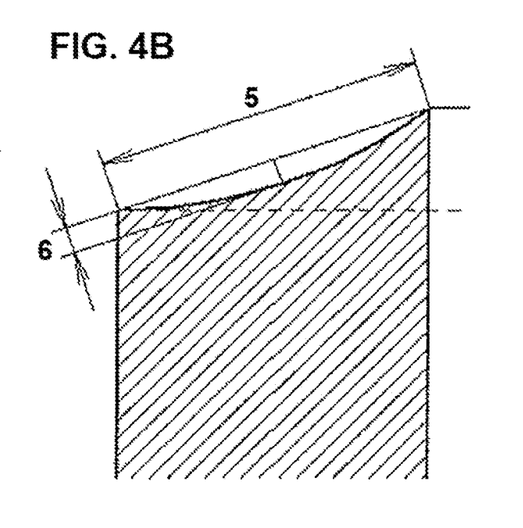
FIG. 4B is a transverse cross-sectional view of an end part in the example illustrated in FIG. 3B of the catalyst (A) in the catalyst group of the third and fourth embodiments of the present invention.
Figure 6A:
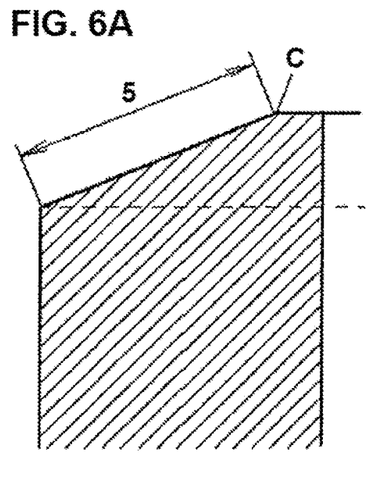
FIG. 6A is a transverse cross-sectional view of an end part in the example illustrated in FIG. 5A of the catalyst (A) in the catalyst group of the third and fourth embodiments of the present invention.
Figure 6B:
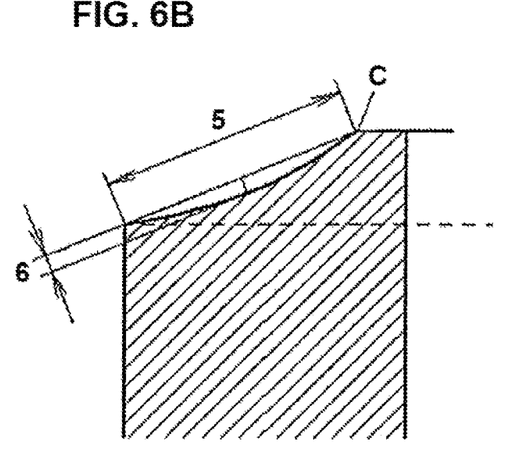
FIG. 6B is a transverse cross-sectional view of an end part in the example illustrated in FIG. 5B of the catalyst (A) in the catalyst group of the third and fourth embodiments of the present invention.
Figure 7:
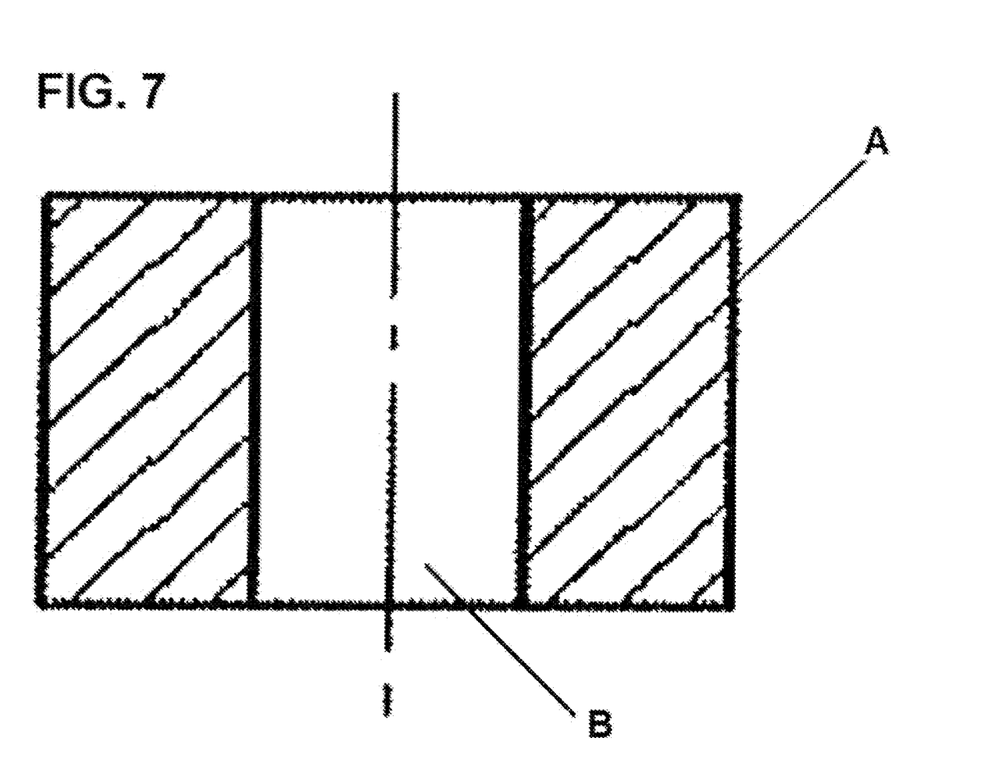
FIG. 7 is a transverse cross-sectional view of a conventional catalyst.

In the catalyst (A), as apparent from FIG. 4B and FIG. 6B, the maximum distance between a surface connecting the end part of the straight body part to the end part of the hollow body part and the concave-curved surface is the length of a portion having a longest distance between the surface connecting the end part of the straight body part to the end part of the hollow body part and the concave-curved surface.

As in the examples of FIG. 4A and FIG. 6A, when the region from the end part of the straight body part to the end part of the hollow body part is linear, the maximum distance between a surface connecting the end pan of the straight body part to the end part of the hollow body part and the concave-curved surface is 0 and therefore, the degree of concave curving is 0 as well.

In the catalyst (A), the region from the end part of the straight body part to the end part of the hollow body part is preferably linear and/or concavely curved at both end parts. In this case, good fluidity is provided to the catalyst group and at the time of filling a reactor such as reaction tube with the catalyst group by means of a funnel, etc., bridging of the catalyst in the funnel is prevented, and uniform filling inside of a reaction tube with the catalyst is achieved, which makes it possible to shorten the filling time. Furthermore, the pressure loss at the time of producing a target substance by gas-phase catalytic oxidation of a raw material substance after filling a reactor such as reaction tube can be reduced, and the target substance can be produced in high yield.

In the catalyst (A), preferable value ranges of the angle between the straight body part and a line connecting the end part of the straight body part to the end part of the hollow body part, the ratio (a/b) of the outer diameter a (mm) to the inner diameter b (mm), the ratio (H/b) of the straight body part length H (mm) to the inner diameter b (mm), the straight body part length H (mm), the outer diameter a (mm), and the ratio (a/H) of the outer diameter a (mm) to the straight body part length H (mm), and reasons therefor are the same as those described for the catalysts of the first and second embodiments.

Similarly to the catalyst of the first embodiment, the catalyst (A) in the catalyst group of the third embodiment is preferably a catalyst containing at least molybdenum and bismuth and is preferably a catalyst represented by the above formula (1).

Similarly to the catalyst of the second embodiment, the catalyst (A) in the catalyst group of the fourth embodiment is preferably a catalyst containing at least molybdenum and vanadium and is preferably a catalyst represented by the above formula (2).

Preferable production methods for these are also the same as those described for the catalysts of the first and second embodiments.

The catalyst groups of the third and fourth embodiments may contain a catalyst having a shape other than the ring shape, and the shape other than the ring shape includes, for example, a spherical shape, a cylindrical shape, etc.

The catalyst groups of the third and fourth embodiments can exert the effects even when they are diluted with an inert filler and used for a gas-phase catalytic oxidation reaction of a raw material substance to produce a target substance. The inert filling material may be sufficient if it is a material which does not cause an unnecessary side reaction during the gas-phase catalytic oxidation reaction, and, for example, a high-temperature treated oxide such as alumina, zirconia, titania, magnesia and silica, or a high-temperature sintered material such as steatite, mullite, silicon carbide and silicon nitride, can be used.

EXAMPLES

Although the present invention is described more specifically below by referring to Examples, the present invention is not limited to the following Examples as long as its gist is observed.

Examples 1-1 to 1-6

<Preparation of Catalyst>

In a vessel, 1,090 ml of warm water was put, and 110 g of ammonium paramolybdate was added and dissolved to form a solution. Subsequently, 407 g of a dispersion of fumed silica in water was added to the solution and stirred to form a suspension (hereinafter, referred to as "suspension A"). As for the dispersion of fumed silica in water, 5 kg of fumed silica (specific surface area: 50 $m^2/g$) was added to 22.5 L of ion-exchanged water to form a fumed silica suspension, and the fumed silica suspension was dispersion-treated for 30 minutes by a homogenizer, ULTRA-TURRAX T115KT (manufactured by IKA) to form a dispersion of fumed silica in water. The resulting dispersion was used as a silicon supply source compound.

In a separate vessel, 127 ml of pure water was put, and 15.1 g of ferric nitrate, 65.7 g of cobalt nitrate and 52.5 g of nickel nitrate were added and dissolved under heating (hereinafter, referred to as "solution B"). The solution B was added to the suspension A, and the mixture was stirred to make the system uniform and heated/dried to obtain a solid. Subsequently, the solid was heat-treated at 300° C. for 1 hour in an air atmosphere.

Furthermore, 110 ml of pure water and 12 ml of ammonia water were put in a separate vessel, and 19.2 g of ammonium paramolybdate was added and dissolved to form a "solution C". Subsequently, 1.7 g of borax and 0.5 g of potassium nitrate were added to the solution C and dissolved to form a "solution D", and 150 g of the heat-treated solid above was added to the solution D and mixed to make the system uniform. Thereafter, 17.4 g of bismuth subcarbonate containing 0.53% Na as a solid solution was added, mixed for 30 minutes, and then heated/dried so as to remove water, and a dry product was thereby obtained. The dry product was pulverized, and the obtained powder was tablet-molded into various shapes to make a ring-shaped molded article having a density of 1.27 $g/cm^3$. The molded article was fired at 515° C. for 2 hours in an air atmosphere and using the obtained ring-shaped catalyst, the catalyst groups of Examples 1-1 to 1-6 were obtained. In this connection, all of the catalysts constituting the catalyst groups of Examples 1-1 to 1-6 have the same composition, and the composition is shown in Table 1.

All of the catalysts constituting a catalyst group of Example 1-1 were free of a bottom surface part as illustrated in FIG. 3A and FIG. 3B and had outer diameter: 5 mm, inner diameter: 2 mm, straight body part length: 3 mm, and hollow body part length: 4 mm. In addition, at both end parts, a region from an end part of a straight body part to an end part of a hollow body part was linear. Furthermore, at both end parts, an angle between the straight body part and a line connecting the end part of the straight body part to the end part of the hollow body part, i.e., the angle between an extension line drawn along the straight body part and a line connecting the end part of the straight body part to the end part of the hollow body part, was 72°.

All of the catalysts constituting a catalyst group of Example 1-2 were free of a bottom surface part as illustrated in FIG. 3A and FIG. 3B and had outer diameter: 5 mm, inner diameter: 2 mm, straight body part length: 3 mm, and hollow body part length: 4 mm. In addition, at one end part, a region from an end part of the straight body part to an end part of the hollow body part was linear, and at another end part, a region from an end part of the straight body part to an end part of the hollow body pan was concavely curved. Namely, the proportion of concave curve in the catalyst group of Example 1-2 was 50%. Furthermore, the distance between the end part of the straight body part and the end part of the hollow body part was 1.59 mm, and a maximum distance between a flat surface connecting the end part of the straight body part to the end pan of the hollow body part and the concave-curved surface was 0.09 mm. Moreover, a ratio of the maximum distance between a surface connecting the end part of the straight body part to the end part of the hollow body part and the concave-curved surface to the distance between the end part of the straight body part and the end part of the hollow body part was 0.06.

All of the catalysts constituting a catalyst group of Example 1-3 were free of a bottom surface part as illustrated in FIG. 3A and FIG. 3B and had outer diameter: 5 mm, inner diameter: 2 mm, straight body part length: 3 mm, and hollow body pan length: 4 mm. In addition, at both end parts, a region from an end part of the straight body part to an end part of the hollow body pan was concavely curved, namely, a proportion of concave curve in the catalyst group of Example 3 was 100%. Furthermore, the ratio of the maximum distance between a surface connecting the end part of the straight body part to the end pan of the hollow body part and the concave-curved surface to the distance between the end part of the straight body pan and the end part of the hollow body pan was 0.1.

All of the catalysts constituting a catalyst group of Example 1-4 were free of a bottom surface part as illustrated in FIG. 3A and FIG. 3B and had outer diameter: 5 mm, inner diameter: 2 mm, straight body part length: 3 mm, and hollow body part length: 4 mm. In the catalysts constituting the catalyst group of Example 1-4, those in which at both end parts, a region from an end part of the straight body part to an end part of the hollow body part is linear, and those in which the region is concavely curved, were mixed and with respect to the catalyst in which the region is concavely curved, a ratio of the maximum distance between a surface connecting the end pan of the straight body pan to the end part of the hollow body part and the concave-curved surface to a distance between the end part of the straight body part and the end part of the hollow body part was 0.1. The proportion of concave curve in the catalyst group of Example 1-4 was 75%.

All of the catalysts constituting a catalyst group of Example 1-5 were free of a bottom surface part as illustrated in FIG. 3A and FIG. 3B and had outer diameter: 5 mm, inner diameter: 2 mm, straight body part length: 3 mm, and hollow body part length: 4 mm. In the catalysts constituting the catalyst group of Example 1-5, those in which at both end parts, a region from an end part of the straight body part to an end part of the hollow body part is linear, and those in which a region is concavely curved, were mixed and with respect to the catalyst in which the region is concavely curved, a ratio of the maximum distance between a surface connecting the end part of the straight body part to the end part of the hollow body part and the concave-curved surface to the distance between the end part of the straight body part and the end part of the hollow body part was 0.1. A proportion of concave curve in the catalyst group of Example 1-5 was 80%.

All of the catalysts constituting a catalyst group of Example 1-6 were the same as the catalyst of Example 1-1 except that outer diameter: 5 mm, inner diameter: 2 mm, straight body part length: 3 mm, and hollow body part length: 3 mm, in which the straight body part length and the hollow body part length were the same and the end part of the straight body part was leveled with the end part of the hollow body part.

<Measurement of Pressure Loss>

An acrylic resin-made straight tube having an inner diameter 26 mm and a length of 1,000 mm was stand straight and filled with the catalyst group of Example 1-1 to a height of 900 mm, dry air was flowed therethrough at a flow rate of 50 NL/min at room temperature from a SUS-made pipe having an inner diameter of 6 mm attached to the upper part of the acrylic resin-made straight tube, and the pressure difference was measured by a digital differential pressure gauge, testo 506-3, attached to a pipe branching off from the SUS-made pipe (differential pressure A). Subsequently, the ring-shaped catalysts were withdrawn from the acrylic resin-made straight tube to provide an empty cylinder, and the pressure difference was measured in the same manner and taken as a blank value. The pressure loss was determined as (differential pressure A)–blank value. In addition, the catalyst groups of Examples 1-2 to 1-6 were measured in the same manner. The measurement results are shown in Table 2.

Here, the number of catalysts constituting the catalyst group filled was as follows:
 Example 1-1: 4,090;
 Example 1-2: 4,014;
 Example 1-3: 4,108;
 Example 1-4: 4,074;
 Example 1-5: 4,091; and
 Example 1-6: 5.014.

<Gas-Phase Catalytic Oxidation Reaction of Propylene>

A mixture prepared by mixing 40 ml of the catalyst group of Example 1-1 and 52 ml of mullite balls having a diameter of 5 mm was filled into a stainless steel-made niter jacket-equipped reaction tube having an inner diameter of 15 mm. A raw material gas containing 10 vol % of propylene, 17 vol % of steam, and 73 vol % of air was flowed at 70 kPa from an inlet of the reaction tube and passed for a contact time of 6.0 seconds with the catalyst group to conduct an oxidation reaction of propylene. In this connection, the reaction tube was heated in a niter bath, and the reaction was conducted at a bath temperature of 320° C. or 330° C. The analysis of the reaction product was conducted in a usual manner by collecting the reaction product from an outlet of the reaction tube and using gas chromatography. In addition, with respect to the catalyst groups of Examples 1-2 to 1-6, the measurement was performed in the same manner. The measurement results are shown in Table 2.

Here, the number of catalysts constituting 40 ml of the catalyst group of each Example was as follows:
 Example 1-1: 322;
 Example 1-2: 315;
 Example 1-3: 322;
 Example 1-4: 319;
 Example 1-5: 318; and
 Example 1-6: 359.

In this connection, the niter is a heating medium composed of a nitrate of alkali metal, and this heating medium melts at 200° C. or more, can be used up to 400° C., has good heat removal efficiency and therefore, is suitable for an oxidation reaction generating a large amount of heat.

Definitions of propylene conversion rate, acrolein yield, acrylic acid yield, and total yield are as follows.

Propylene conversion rate (mole)=(molar number of reacted propylene/molar number of supplied propylene)×100

Acrolein yield (mol %)=(molar number of produced acrolein/molar number of supplied propylene)×100

Acrylic acid yield (mol %)=(molar number of produced acrylic acid/molar number of supplied propylene)×100

Total yield (mol %)=acrolein yield (mol %)+acrylic acid yield (mol %)

TABLE 1

| Catalyst Composition (atomic ratio) | | | | | | | | |
|---|---|---|---|---|---|---|---|---|
| Mo | Bi | Co | Ni | Fe | Na | K | B | Si |
| 12 | 1 | 3 | 3 | 1 | 0.3 | 0.1 | 0.4 | 21 |

TABLE 2

| | Upward | | Bath Temperature 330° C. | | | | |
|---|---|---|---|---|---|---|---|
| | Ratio by Shaking Test (%) | Pressure Loss (hPa) | Propylene Conversion Rate (mol %) | Acrolein Selectivity (mol %) | Acrylic Acid Selectivity (mol %) | Total*[1] Selectivity (mol %) | Total*[2] Selectivity (mol %) |
| Example 1-1 | 1 | 43 | 99.3 | 69.5 | 21.6 | 91.1 | 90.5 |
| Example 1-2 | 3 | 39 | 99.3 | 71.3 | 19.9 | 91.2 | 90.6 |
| Example 1-3 | 23 | 37 | 99.0 | 72.5 | 20.3 | 92.8 | 91.9 |
| Example 1-4 | 18 | 38 | 99.2 | 74.3 | 17.9 | 92.2 | 91.5 |
| Example 1-5 | 20 | 37 | 99.1 | 74.8 | 17.6 | 92.4 | 91.6 |
| Example 1-6 | 93 | 51 | 99.2 | 70.7 | 20.0 | 90.7 | 90.1 |

*[1]A total of acrolein selectivity and acrylic acid selectivity.
*[2]A total of acrolein yield and acrylic acid yield, and the yield is a value obtained by multiplying conversion rate by selectivity.

In the case where acrolein and/or acrylic acid were produced from propylene by using a reactor filled with each of the catalyst groups of Examples 1-1 to 1-5 satisfying the requirements of the catalyst group of the third embodiment of the present invention, the pressure loss was kept low and the propylene conversion rate was high, as a result, acrolein and/or acrylic acid could be produced in high yield. With the catalyst groups of Examples 1-2 to 1-5 using the catalyst of the first embodiment of the present invention, among others, the pressure loss could be kept particularly low.

Examples 2-1 to 2-4

<Preparation of Catalyst>

A composite metal oxide in which the empirical formula of the constituent components excluding oxygen is the composition shown in Table 3 was produced as follows.

Basic nickel carbonate was dispersed in 350 ml of pure water, and silica and antimony trioxide were added thereto, followed by thorough stirring.

The resulting slurry-like solution was concentrated by heating and dried. The obtained dry solid was fired at 800° C. for 3 hours in a muffle furnace, and the produced solid was pulverized to obtain a powder capable of passing through a 60-mesh sieve (Sb—Ni—Si—O powder).

On the other hand, pure water was heated to 80° C., and ammonium paramolybdate and ammonium metavanadate were sequentially dissolved under stirring. An aqueous copper sulfate solution prepared by dissolving copper sulfate in 100 ml of pure water was added thereto, and niobium hydroxide was further added. The resulting mixture was stirred to obtain a slurry solution.

The Sb—Ni—Si—O powder obtained above was gradually added to the slurry solution under stirring, and the solution was thoroughly stirred and mixed. The resulting slurry-like solution was spray-dried at 150° C. to obtain a precursor compound. Thereto, 1.5 wt % of graphite was added and mixed, and the mixture was molded into a ring shape having a density of 2.93 g/cm$^3$ by means of a small tablet-molding machine. The resulting molded body was fired at 380° C. in a 1% oxygen flow, and using the obtained ring-shaped catalyst, the catalyst groups of Examples 2-1 to 2-4 were obtained.

All of the catalysts constituting the catalyst group of Example 2-1 were free of a bottom surface part as illustrated in FIG. 3A and FIG. 3B and had outer diameter: 5 mm, inner diameter: 2 mm, straight body part length: 3 mm, and hollow body part length: 4 mm. In addition, at both end parts, a region from an end part of the straight body part to an end pan of the hollow body part was linear. Furthermore, at both end parts, an angle between the straight body part and a line connecting the end part of the straight body part to the end pan of the hollow body part, i.e., the angle between an extension line drawn along the straight body part and a line connecting the end part of the straight body part to the end part of the hollow body part, was 72°.

All of the catalysts constituting the catalyst group of Example 2-2 were free of a bottom surface part as illustrated in FIG. 3A and FIG. 3B and had outer diameter: 5 mm, inner diameter: 2 mm, straight body part length: 3 mm, and hollow body part length: 4 mm. In addition, at both end parts, a region from an end part of the straight body part to an end pan of the hollow body part was concavely curved. Namely, the proportion of concave curve in the catalyst group of Example 2-2 was 100%. Furthermore, a distance between an end part of the straight body part and an end part of the hollow body part was 1.59 mm, and a maximum distance between a flat surface connecting the end part of the straight body part to the end pan of the hollow body part and the concave-curved surface was 0.10 mm. Moreover, a ratio of the maximum distance between a surface connecting the end part of the straight body part to the end part of the hollow body pan and the concave-curved surface to the distance between the end part of the straight body part and the end part of the hollow body part was 0.06. Furthermore, at both end parts, an angle between the straight body part and a line connecting the end part of the straight body part to the end part of the hollow body part, i.e., the angle between an extension line drawn along the straight body part and a line connecting the end part of the straight body part to the end pan of the hollow body part, was 72°.

All of the catalysts constituting the catalyst group of Example 2-3 were free of a bottom surface part as illustrated in FIG. 3A and FIG. 3B and had outer diameter: 5 mm, inner diameter: 2 mm, straight body part length: 3 mm, and hollow body part length: 4 mm. In addition, a distance between an end part of the straight body part and an end part of the hollow body part was 1.59 mm. Furthermore, at both end parts, an angle between the straight body part and a line connecting the end part of the straight body part to the end part of the hollow body part, i.e., the angle between an extension line drawn along the straight body part and a line connecting the end pan of the straight body pan to the end part of the hollow body part, was 72°. In the catalysts constituting the catalyst group of Example 2-3, those in which at both end parts, a region from an end part of the straight body part to an end part of the hollow body part is linear, and those in which the region is concavely curved were mixed, and with respect to the catalyst in which the region is concavely curved, a maximum distance between a surface connecting the end part of the straight body part to the end part of the hollow body part and the concave-curved surface was 0.10 mm, and a ratio of the maximum distance between a surface connecting the end part of the straight body part to the end part of the hollow body part and the concave-curved surface to the distance between the end part of the straight body part and the end part of the hollow body part was 0.06. A proportion of concave curve in the catalyst group of Example 2-3 was 75%.

The catalyst of Example 2-4 had outer diameter: 5 mm, inner diameter: 2 mm, straight body part length: 3 mm, and hollow body part length: 3 mm, in which the straight body part length and the hollow body part length were the same as illustrated in FIG. 5A and FIG. 5B and the end part of the straight body part was leveled with the end part of the hollow body part.

<Measurement of Pressure Loss>

The pressure loss was measured by the same method as in Examples 1-1 to 1-6. The measurement results are shown in Table 4.

Here, the number of catalysts constituting the catalyst group filled was as follows:
Example 2-1: 3,935:
Example 2-2: 3,847;
Example 2-3: 3,748; and
Example 2-4: 5,020.

<Gas-Phase Catalytic Oxidation Reaction of Acrolein>

A reaction tube (inner diameter: 21 mm) with a jacket containing niter was filled with 30 ml of the catalyst group of Example 2-1, and a gas-phase catalytic oxidation reaction of acrolein was conducted by heating the reaction tube, introducing a composition gas (acrolein: 6 vol %, oxygen: 8 vol %, steam: 22 vol %, nitrogen gas: 64 vol %), and setting SV (space velocity: flow rate of raw material gas per unit time/apparent volume of catalyst filled) at 1,550/hr. In addition, with respect to the catalyst groups of Examples 2-2 to 2-4, the measurement was performed in the same manner. The measurement results are shown in Table 4.

Here, the number of catalysts constituting 30 ml of the catalyst group of each Example was as follows:
Example 2-1: 266;
Example 2-2: 260;
Example 2-3: 253; and
Example 2-4: 298.

Definitions of acrolein conversion rate, acrylic acid selectivity, and acrylic acid yield are as follows:

Acrolein conversion rate (mol %)=100×(molar number of reacted acrolein)/(molar number of supplied acrolein);

Acrylic acid selectivity (mol %)=100×(molar number of produced acrylic acid)/(molar number of converted acrolein); and Acrylic acid yield (mol %)=100×(molar number of produced acrylic acid)/(molar number of supplied acrolein).

TABLE 3

| Catalyst Composition (atomic ratio) | | | | | | |
|---|---|---|---|---|---|---|
| Mo | V | Nb | Cu | Ni | Sb | Si |
| 12 | 2.4 | 1.0 | 1.2 | 8.5 | 20 | 2 |

TABLE 4

| | Upward Ratio by Shaking Test (%) | Pressure Loss (hPa) | Reaction Temperature (° C.) | Acrolein Conversion Rate (mol %) | Acrylic Acid Selectivity (mol %) | Acrylic Acid Yield (mol %) |
|---|---|---|---|---|---|---|
| Example 2-1 | 1 | 43 | 240 | 99.6 | 93.5 | 93.1 |
| Example 2-2 | 14 | 37 | 240 | 99.8 | 93.5 | 93.3 |
| Example 2-3 | 13 | 38 | 240 | 99.7 | 93.6 | 93.3 |
| Example 2-4 | 93 | 51 | 240 | 99.5 | 93.4 | 92.9 |

In the case where a gas-phase catalytic oxidation reaction of acrolein which is an unsaturated aldehyde was conducted by using a reactor filled with each of the catalyst groups of Examples 2-1 to 2-3 satisfying the requirements of the catalyst group of the fourth embodiment of the present invention to produce acrylic acid which is a corresponding unsaturated carboxylic acid, a pressure loss was kept low, and the acrolein could be oxidized at a high conversion rate without raising a temperature, by which acrylic acid could be produced in high yield. With the catalyst groups of Examples 2-2 and 2-3 using the catalyst of the second embodiment of the present invention, among others, the pressure loss could be kept particularly low.

The pressure loss in Examples above was simply measured by setting the catalyst packed layer length to 900 mm and flowing dry air at a gas flow velocity of 50 NL/min and shows superiority over conventional techniques. In this connection, usually, the pressure loss is in general proportional to the catalyst packed layer length and the square of gas flow velocity as evidenced in the following Ergun equation. In industrially producing a target substance, a fixed-bed tubular reactor is used and, usually, the fixed-bed tubular reactor has from several thousands to several tens of thousands of reaction tubes of 2,000 to 7,000 mm length (JP-A-2011-225476, International Publication No. 2005/005037). Consequently, in the production plant of a target substance, the difference of the pressure loss of the present invention from those in conventional techniques tends to be as large as 2.2 to 7.8 times of the results shown in Examples, and therefore it is apparent that the superiority of the present invention is higher as the reaction grows in size to an industrial scale. Furthermore, in the production of a target substance, coking is likely to occur as the pressure loss is higher, and a rise in the pressure loss and an increase of coking occur over time. Namely, it is apparent that as time goes by, the difference of the pressure loss of the present invention from those of conventional techniques tends to be widened.

$$\frac{\Delta P}{L} = \left(\frac{\rho u^2}{D_p}\right)\left(\frac{1-\varepsilon}{\varepsilon^3}\right)\left(\frac{150}{Re_p} + 1.75\right) \text{ Ergun equation} \qquad [\text{Math. 1}]$$

($\Delta P$: pressure loss, L: packed layer length, $\rho$: gas density: u: gas flow velocity, Dp: particle diameter, $\varepsilon$: void ratio: Rep: Reynolds number).

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-061962) filed on Mar. 27, 2017, Japanese Patent Application (Patent Application No. 2017-088648) filed on Apr. 27, 2017, Japanese Patent Application (Patent Application No. 2017-097655) filed on May 16, 2017, Japanese Patent Application (Patent Application No. 2017-097656) filed on May 16, 2017, Japanese Patent Application (Patent Application No. 2018-012547) filed on Jan. 29, 2018, Japanese Patent Application (Patent Application No. 2018-012548) filed on Jan. 29, 2018, Japanese Patent Application (Patent Application No. 2018-012549) filed on Jan. 29, 2018, and Japanese Patent Application (Patent Application No. 2018-012550) filed on Jan. 29, 2018, the entirety of which is incorporated herein by way of reference. All references cited herein are incorporated by reference in their entirety.

REFERENCE SIGNS LIST

1: Inner diameter b
2: Outer diameter a
3: Straight body part length H
4: Angle between straight body part and a line connecting end part of straight body part to end part of hollow body part
5: Distance between end part of straight body part and end part of hollow body part
6: Maximum distance between surface connecting end part of straight body part to end part of hollow body part and concave-curved surface
7: Hollow body part length
A: Straight body part
B: Hollow body part
C: End part of hollow body part

The invention claimed is:
1. A catalyst group, comprising:
200 or more ring-shaped catalysts, each having a straight body part and a hollow body part, which is suitable for a gas-phase catalytic oxidation reaction of an olefin or a tertiary butanol to produce a corresponding unsaturated aldehyde and/or unsaturated carboxylic acid, wherein the catalyst group satisfies (1) and (2):
(1) the catalyst group comprises a catalyst (A) in which a length of the straight body part is shorter than a length of the hollow body part, the straight body part is present between a surface comprising a first end part of the hollow body part and a surface comprising a second end part of the hollow body part, and at least at one end part, a region from an end part of the straight body part to an end part of the hollow body part is linear and/or concavely curved; and
(2) an upward ratio by a shaking test of the catalyst group is 70% or less,
wherein a number ratio of the catalyst (A) to the ring-shaped catalysts is at least 10%,
wherein a proportion of concave curve in the region of the catalyst (A) is at least 40% of a total number of the first end part and the second end part with a remainder being linear, and
wherein the upward ratio is measured by a shaking test of the catalyst group, involving randomly selecting 100 ring-shaped catalysts from the catalyst group and placing the 100 ring-shaped catalysts in a stainless steel tray having a width of 296 mm, a depth of 231 mm, and a height of 49 mm, mounting the stainless steel tray in a digital shaker, and, after shaking for 1 minute at a reciprocatory shaking width of 10 mm and a shaking speed of 350 reciprocations/min, defining a number of the ring-shaped catalysts having an upward hollow body part per 100 ring-shaped catalysts as the upward ratio.

2. The catalyst group of claim 1, wherein, in the catalyst (A), a ratio of a maximum distance in mm between a surface connecting the end part of the straight body part to the end part of the hollow body part and the linear or concavely curved surface to a distance in mm between the end part of the straight body part and the end part of the hollow body part is 0 or more and 0.2 or less.

3. The catalyst group of claim 1, wherein at both end parts of the catalyst (A), the region from the end part of the straight body part to the end part of the hollow body part is linear and/or concavely curved.

4. The catalyst group of claim 1, wherein the proportion of the concave curve in the region of the catalyst (A) is 50% or more.

5. The catalyst group of claim 1, wherein the proportion of the concave curve in the region of the catalyst (A) is 60% or more.

6. The catalyst group of claim 1, wherein the proportion of the concave curve in the region of the catalyst (A) is 70% or more.

7. The catalyst group of claim 1, wherein the proportion of the concave curve in the region of the catalyst (A) is 80% or more.

8. The catalyst group of claim 1, wherein the proportion of the concave curve in the region of the catalyst (A) is 90% or more.

9. The catalyst group of claim 1, wherein the proportion of the concave curve in the region of the catalyst (A) is 95% or more.

10. The catalyst group of claim 1, wherein the number ratio of the catalyst (A) to the ring-shaped catalysts is at least 50%.

11. A catalyst group, comprising:

200 or more ring-shaped catalysts, each having a straight body part and a hollow body part, which is suitable for gas-phase catalytic oxidation of an unsaturated aldehyde to produce a corresponding unsaturated carboxylic acid, wherein the catalyst group satisfies (1) and (2):

(1) the catalyst group comprises a catalyst (A) in which the length of the straight body part is shorter than the length of the hollow body part, the straight body part is present between a surface comprising a first end part of the hollow body part and a surface comprising a second end part of the hollow body part, and at least at one end part, the region from an end part of the straight body part to an end part of the hollow body part is linear and/or concavely curved; and (2) an upward ratio by a shaking test of the catalyst group is 70% or less, wherein a number ratio of the catalyst (A) to the ring-shaped catalysts is at least 10%, wherein a proportion of concave curve in the region of the catalyst (A) is at least 40% of a total number of the first end part and the second end part with a remainder being linear, and wherein the upward ratio is measured by a shaking test of the catalyst group, involving randomly selecting 100 ring-shaped catalysts from the catalyst group and placing the 100 ring-shaped catalysts in a stainless steel tray having a width of 296 mm, a depth of 231 mm, and a height of 49 mm, mounting the stainless steel tray in a digital shaker, and, after shaking for 1 minute at a reciprocatory shaking width of 10 mm and a shaking speed of 350 reciprocations/min, defining a number of the ring-shaped catalysts having an upward hollow body part per 100 ring-shaped catalysts as the upward ratio.

12. The catalyst group of claim 11, wherein in the catalyst (A), a ratio of a maximum distance in mm between a surface connecting the end part of the straight body part to the end part of the hollow body part and the linear or concavely curved surface to a distance in mm between the end part of the straight body part and the end part of the hollow body part is 0 or more and 0.2 or less.

13. The catalyst group of claim 11, wherein at both end parts of the catalyst (A), the region from the end part of the straight body part to the end part of the hollow body part is linear and/or concavely curved.

14. The catalyst group of claim 11, wherein the proportion of the concave curve in the region of the catalyst (A) is 50% or more.

15. The catalyst group of claim 11, wherein the proportion of the concave curve in the region of the catalyst (A) is 60% or more.

16. The catalyst group of claim 11, wherein the proportion of the concave curve in the region of the catalyst (A) is 70% or more.

17. The catalyst group of claim 11, wherein the proportion of the concave curve in the region of the catalyst (A) is 80% or more.

18. The catalyst group of claim 11, wherein the proportion of the concave curve in the region of the catalyst (A) is 90% or more.

19. The catalyst group of claim 11, wherein the proportion of the concave curve in the region of the catalyst (A) is 95% or more.

20. The catalyst group of claim 11, wherein the number ratio of the catalyst (A) to the ring-shaped catalysts is at least 50%.

* * * * *